United States Patent
Rigal et al.

(10) Patent No.: US 8,080,242 B2
(45) Date of Patent: Dec. 20, 2011

(54) ANTI-HPA

(75) Inventors: Dominique Rigal, St Didier au Mt d'Or (FR); Jean Jacques Pin, St Bonnet de Mure (FR); Yves Merieux, Lyons (FR)

(73) Assignee: Stiftung Für Diagnostische Forschung, Cressier sur Morat (CH)

( * ) Notice: Subject to any disclaimer, the term of this patent is extended or adjusted under 35 U.S.C. 154(b) by 233 days.

(21) Appl. No.: 12/139,086

(22) Filed: Jun. 13, 2008

(65) Prior Publication Data

US 2009/0117128 A1    May 7, 2009

(30) Foreign Application Priority Data

Jun. 22, 2007    (EP) ..................................... 07012282

(51) Int. Cl.
*A61K 39/395*    (2006.01)
*C07K 16/36*    (2006.01)
*C07K 16/18*    (2006.01)
*C12P 21/08*    (2006.01)

(52) U.S. Cl. ............... 424/130.1; 424/141.1; 424/152.1; 435/975; 530/387.1; 530/388.1; 530/388.7

(58) Field of Classification Search .................. None
See application file for complete search history.

(56) References Cited

U.S. PATENT DOCUMENTS

| | | | | |
|---|---|---|---|---|
| 5,516,634 A | * | 5/1996 | Newman et al. | 435/6 |
| 5,955,266 A | * | 9/1999 | Bray et al. | 435/6 |
| 6,210,904 B1 | * | 4/2001 | Bednar et al. | 435/7.1 |
| 2003/0027207 A1 | * | 2/2003 | Filpula | 435/7.1 |

OTHER PUBLICATIONS

Feyron et al, J Immunology 153: 1333-1339, 1994.*
Sanz et al, Transfusion 41: 762-765, Jun. 2001.*
Moncharmont et al, Immuno-Analyse et Biologie Specialisee 18(3): 140-143, Jun. 2003.*

* cited by examiner

*Primary Examiner* — Phuong Huynh
(74) *Attorney, Agent, or Firm* — McDonnell Boehnen Hulbert & Berghoff LLP (57) ABSTRACT

The present invention relates to a monoclonal antibody selectively recognizing a human platelet alloantigen, a method for detecting the presence or absence of at least one human platelet alloantigen using said antibody, a method for the production of said antibody, a pharmaceutical composition comprising said antibody, and a kit containing said antibody.

3 Claims, 6 Drawing Sheets

ANTI-HPA

BACKGROUND OF THE INVENTION

Antibodies against platelet alloantigens play an important role in immune mediated disorders. HPA-1 and HPA-5 are the most important platelet alloantigens related to pathological situations. The approximate genotype frequencies in Caucasians for HPA-5 are 79.4% HPA-5aa, 19.4%, HPA-5ab, 1.2% HPA-5bb. Consequently, a considerable proportion of the population is at risk of being immunized by the HPA-5 antigen either after pregnancy or transfusion. The alloantigen containing the differences between the two allelic forms of HPA-5 is located on the glycoprotein Ia (GPIa) which is non-covalently associated with GPIIa. The HPA-5b allele contains an adenine instead of guanine at base 1648, which results in a glutamic acid to lysine amino acid substitution responsible for immunological distinction of the two alleles. GPIa/IIa (VLA-2, CD49b/CD29) is a member of the integrin family of adhesion receptors involved in cell-cell and cell-matrix interactions. Functionally GPIa contains a collagen binding site. If blood vessels become damaged, collagen in the subendothelium is exposed. As an important physiological activator of platelets, the collagen binding to GPIa/IIa leads to the induction of aggregation and adhesion.

Alloantibodies against HPA-5b on GPIa/IIa were first found in cases of neonatal alloimmune thrombocytopenia (NAIT) and in sera from polytransfused patients. In our hands development of NAIT caused by an alloimmunisation against HPA-5b is approximately as frequent as against HPA-1a, although clinical symptoms are often less severe. The incidence of NAIT is 1.3 per 1000 live births. The risk of morbidity is significant: 20% of affected infants have neurologic sequelae and the death rate is about 10%. Most cases of NAIT are caused by immunization of the mother against the platelet-specific alloantigen HPA-1a (80% of NAIT cases), and the remaining cases are caused predominantly by anti-HPA-5b response. Allo-anti-HPA-5b are more frequent than allo-anti-HPA-1a in case of platelet refractoriness. In other studies the frequency of anti HPA-5b alloantibodies is much higher. In the Lyon Blood Center the frequency of anti HPA-5b is 90%. Even low levels of alloantibodies as induced in mild or subclinic cases of NAIT lead to immunological memory, known to increase the risk of posttransfusion purpura (PTP) for years after delivery. The clinical course of PTP is characterized by pronounced thrombocytopenia and severe hemorrhagic diathesis about one week after the responsible transfusion. Serious complications related to platelet alloantigens are not only found in situations of alloincompatibility in pregnancy, but also in polytransfused patients and even in cases of bone marrow transplantation. Taken together, these clinical complications emphasise the need for routine platelet typing in parallel with the routine typing for the AB0 blood group system. For this reason and for detection of platelet alloantibodies, a simple and reliable diagnostic assay, that is suitable for widespread use and not only performed by a few reference laboratories, is required.

Up to now, the phenotyping for HPA-5b has been dependent on the availability of rare polyclonal human sera containing platelet specific alloantibodies. Most of these sera, however, are impaired by the presence of alloantibodies especially against HLA class I antigens and have to be submitted to extensive absorption and purification protocols. Furthermore, the quality of these antisera is subject to high batch-to-batch variation due to the fluctuations of antibody titers in donor sera.

Recently, a specific human alloantibody against HPA-1a on GPIIb/IIIa was isolated by phage display technology and produced as full-length IgG1 antibody. For the selection of anti-HPA-1a specific phages the purified GPIIb/IIIa was available. The IIb/IIIa containing the HPA-1 is expressed at 50 000 to 80 000 copies per platelet, whereas expression of GPIa/IIa with the HPA-5 is 100 fold lower (800 to 2800 copies per platelet). Due to this low expression it was extremely difficult to purify enough GPIa/IIa which could then be used for the selection of anti-HPA-5b specific Fab-phages. It is why this technology is inefficient to produce anti HPA-5b monoclonal antibody.

Further, establishing a platelet typed blood product panel is complicated by current phenotyping assays that require potent polyclonal anti-HPA-5b sera. Also, the Monoclonal Antibody-specific Immobilization of Platelet Antigens (MAIPA) assay, as a standard method for the detection of alloantibodies in serum and plasma and used to phenotype platelets, is dependent on polyclonal antisera. The polyclonal antisera are rare and dependent on the blood donations from women alloimmunized by their babies. Furthermore the use of such sera may be impaired by the presence of antibodies against other polymorphic antigens such as the AB0 blood groups or HLA. Complicated absorption and purification protocols are required before the polyclonal antiserum is suitable for use in diagnostic assays.

Thus, the problem underlying the present invention is to provide new means for detecting human platelet alloantigens The solution to the above technical problem is achieved by the embodiments characterized in the claims.

SUMMARY OF THE INVENTION

The present invention relates to a monoclonal antibody selectively recognizing a human platelet alloantigen, a method of detecting the presence or absence of at least one human platelet alloantigen using said antibody, a method for the production of said antibody, a pharmaceutical composition comprising said antibody, and a kit containing said antibody.

BRIEF DESCRIPTION OF THE DRAWINGS

FIG. 1 illustrates that the HF2H11 human antibody is specific for HPA 5b allele present on human platelets in a ELISA test. We evaluated 60 samples known for HPA 5a or 5b genotypes. This test shows no discrepancy between phenotyping and genotyping.

FIG. 4 illustrates the performance of anti-HPA-5b in the MAIPA assay. The MAIPA assay was performed to test the specificity of recombinant anti-HPA-5b antibody on platelets typed for HPA-5a and HPA-5b from different donors. Mouse monoclonal anti-human GPIa/IIa was incubated with typed platelets and anti-HPA-5b. Platelets were lysed and immobilized by goat anti-mouse IgG bound on plate. After Washing, bound anti-HPA-5b was detected by anti-HuIgG-HRP. Absorbance was read at λ=490 nm. No signal was detectable on HPA-5aa platelets. 50 donors and 10 Panel platelets tested in 2 techniques; 38 donors genotyped HPA-5b negative and 12 HPA-5b positive 3 panel platelets known HPA-5b negative, 7 HPA-5b positive.

DETAILED DESCRIPTION OF THE INVENTION

In particular, the present invention relates to a monoclonal antibody selectively recognizing a human platelet alloantigen (HPA).

The term "antibody" as used herein may be any antibody including biologically active fragments of an antibody having substantially the same biological function as the antibody, e.g. the ability to bind a specific human platelet alloantigen. In particular, the antibody according to the present invention can be an antibody derived by conventional hybridoma techniques, and an antibody or antibody fragment obtained by recombinant techniques, e.g. phage display or ribosome display. In a preferred embodiment of the present invention, the antibody is a monoclonal antibody produced by immortalisation of B lymphocyte technology. In another preferred embodiment of the present invention, the antibody is an alloantibody. In another preferred embodiment of the present invention, the antibody is a human antibody. In another preferred embodiment of the present invention, the monoclonal antibody is a fragment of a monoclonal antibody selectively recognizing a human platelet alloantigen.

The antibody of the present invention may belong to any immunoglobulin class. In a preferred embodiment of the present invention, the monoclonal antibody is primarily IgG but may include IgM and IgA. In a more preferred embodiment of the present invention, the antibody is an IgG1 antibody.

The term "human platelet alloantigen (HPA)" as used herein also relates to any biologically active derivative of a human platelet alloantigen having substantially the same biological function as the respective human platelet alloantigen, e.g. a fragment or hapten of a human platelet alloantigen having substantially the same biological properties. In a preferred embodiment of the present invention, the HPA is HPA-5. In a more preferred embodiment of the present invention, the HPA is HPA-5b.

The present invention further relates to a method for the detection of at least one human platelet alloantigen, comprising the steps of bringing a system containing at least one human platelet alloantigen into contact with a system containing at least one antibody as defined above.

Additionally, the present invention relates to a method for detecting the presence or absence of at least one human platelet alloantigen, comprising the steps of (a) incubating a first system containing at least one HPA, and a second system containing at least one antibody as defined above under antibody/antigen-complex forming conditions; and (b) evaluating the antibody/antigen-complex formed in step (a) qualitatively and/or quantitatively.

In a preferred embodiment of the present invention, the HPA is an HPA as defined above.

The first system containing at least one human platelet alloantigen may be any in vitro system containing at least one human platelet alloantigen. In one embodiment of the present invention, the system may be a naturally occurring system such as a solution selected from the group consisting of whole blood, serum, plasma, and tissues. Further, the system may comprise a solution containing at least one platelet derived from naturally occurring systems, e.g. a solution containing isolated blood compounds or processed blood products. In another embodiment of the present invention, the system may comprise cells expressing human platelet alloantigens, e.g. a cell culture system. Methods for obtaining the above systems are known in the prior art.

The incubation of the first system and the second system is carried out under any conditions suitable for antibody/antigen-complex forming without any limitation. This comprises e.g. any suitable buffer system, temperature, time period and agitation of the buffer solution. In a preferred embodiment of the present invention the incubation is carried out at a temperature ranging from about 4° C. to about 37° C. for from about 5 to about 45 minutes. In a more preferred embodiment of the present invention, the incubation is carried out at about room temperature for about 30 minutes.

In one embodiment of the above method one or more antibodies as defined above are immobilized on a solid substrate. In another embodiment of the present invention one or more HPA as defined above are immobilized on a solid substrate. The term "substrate" does not have any specific limitations, and relates, for example, to an insoluble polymer material, which can be an organic polymer, such as polyamide or a vinyl polymer (e.g. poly(meth)acrylate, polystyrene and polyvinyl alcohol, or derivatives thereof, a natural polymer such as cellulose, dextrane, agarose, chitin and polyamino acids, or an inorganic polymer, such as glass or metallohydroxide. The substrate can be in the form of a microcarrier, particles, membranes, strips, paper, film, pearls or plates, such as microtiter plates or microarrays. The term "microarray" as used herein means any arrangement of the antibodies or antigens in addressable locations on a substrate resulting in a so-called "biochip". The antibodies or the antigens can be immobilized on the substrate directly by covalent coupling or via a carrier such as a linker molecule or an antibody immobilized on the substrate.

The antibody/antigen-complex formed can be evaluated qualitatively and/or quantitatively by methods well known in the art. Examples for the evaluation of the above mentioned complex are, but not limited to, for example the evaluation of blood agglutination, flow cytometry, MAIPA test, Western Blot, enzyme linked immuno sorbent assay (ELISA), and other immunoassays, or the use of a labelled antibody directed against the monoclonal antibody selectively recognizing a HPA.

The monoclonal antibody selectively recognizing a HPA according to the present invention may be covalently linked to a detectable label. The term "detectable label" as used herein is not restricted to a special type of detection label, such as biochemical detection marker, but includes any residue known in the art which is suitable for detection.

The detection method for measuring the detectable label can be, for example, selected from the group consisting of an enzyme assay, like e.g. horseradish peroxidase (HRPO), a chromogenic assay, a lumino assay, a fluorogenic assay, and a radioimmune assay. The reaction conditions to perform detection of the detectable label depend upon the detection method selected. It is within the knowledge of the person skilled in the art to choose the optimal parameters, such as buffer system, temperature and pH for the respective detection system to be used. Further, the detection method may comprise one or more detection method(s) selected from the group consisting of immunoblotting, immunoprecipitation, immunocapture, monoclonal antibody immobilization of platelet antigens, ELISA, flow cytometry, protein array technology, spectroscopy, mass spectrometry, chromatography, surface plasmonic resonance, fluorescence extinction, fluorescence energy transfer, evanescence technology and/or total internal reflection fluorimetry.

The present invention further relates to the use of the above method for testing donor blood for a blood transfusion. Moreover, the present invention further relates to the use of the above method for testing recipient blood for a blood transfusion. The term "blood" as used herein includes any blood component and/or blood product suitable for carrying out antibody screening, such as e.g. serum, plasma, or other body fluids or tissues which may contain HPA.

Additionally, the present invention relates to the use of the above method for discriminating the two variant allogeneic forms of a HPA (i.e. a and b), wherein the HPA is a HPA as defined above. This method can be used for determining the phenotype of platelets.

The present invention further relates to a method for the production of a monoclonal antibody selectively recognizing a human platelet alloantigen, comprising the steps of
(a) isolating B lymphocytes producing an anti-HPA-5b antibody;
(b) expanding at least one lymphocyte producing an anti-HPA-5b antibody;
(c) infecting the at least one B lymphocyte with Epstein-Barr Virus;
(d) cloning the at least one B lymphocyte by limiting dilution in presence of feeder cells;
(e) incubating the cloned cells with at least one anti-CD 40 antibody;
(f) identification and cloning of at least one monoclonal cell line;
(g) cultivating of the at least one monoclonal cell line and harvesting the antibody.

The steps of the above method is carried out is carried out under any suitable conditions known in the prior art without any limitation. This comprises e.g. any suitable buffer system, temperature, time period and agitation of the buffer solutions.

In step (a) the B lymphocytes may be for example isolated from any natural occurring source, e.g. blood cells. In step (c) the EBV infection may be carried out e.g. via electroporation or microinjection. The cultivation of the cells in step (g) may be carried out e.g. in a continuous or batchwise manner, the expression of the antibody may be carried out e.g. constitutive or upon induction, and the isolation of the antibody may be carried out, e.g. from the culture medium or by harvesting the transformed cells. In a preferred embodiment of the present invention the antibody is harvested from the supernatant of the cultivated cells. In another preferred embodiment, the antibody is further purified, e.g. via anion exchange chromatography or affinity chromatography.

In a preferred embodiment of the present invention the antibody is an antibody as defined above.

The present invention also relates to a method for the production of a monoclonal antibody selectively recognizing a human platelet alloantigen comprising the steps of ((i) isolating the DNA of at least one B lymphocyte producing an anti-HPA-5b antibody which has been infected with Epstein-Barr Virus and (ii) expressing the monoclonal antibody in a suitable system. The suitable system for expressing a monoclonal antibody may be any suitable system known in the art.

The present invention also relates to an antibody as defined above obtainable by the methods as defined above.

Additionally, the present invention relates to a pharmaceutical composition comprising an antibody as defined above. The present invention further relates to the use of the pharmaceutical composition according to the present invention for the prevention and/or treatment of an alloimmunisation.

The present invention further relates to the use of the antibody as defined above in the prevention and/or treatment of an alloimmunisation.

The present invention further relates to a method of preventing an alloimmunisation of an individual comprising the steps of (a) determining the presence of an HPA in an individual and (b) administering an antibody according to the present invention selectively recognizing said HPA. The present invention also relates to a method of treating an alloimmunisation of an individual comprising the steps of (a) determining the presence of an HPA in an individual and (b) administering an antibody according to the present invention selectively recognizing said HPA. The presence of an HPA can be determined for example by determining the presence of a nucleic acid sequence encoding the HPA in the genome of the individual or by detecting the presence of the HPA in a blood component of the individual. In a preferred embodiment of the present invention, the presence of the HPA is determined using the method for detecting the presence or absence of at least one HPA according to the present invention.

In a preferred embodiment of the present invention, the alloimmunisation is an anti-HPA-5b alloimmunisation.

In another preferred embodiment of the present invention, the alloimmunisation results in a primary hemostatic disorder. In a more preferred embodiment of the present invention, the primary hemostatic disorder is an alloimmune thrombocytopenia, selected from the group consisting of posttransfusion purpura (PTP) and of neonatal alloimmune thrombocytopenia (NAIT).

The antibody according to the present invention inhibits substantially the adhesion of platelets on collagen and inhibits substantially the aggregation of platelets induced by collagen. Therefore, the pharmaceutical composition according to the present invention and/or the antibody according to the present invention may be used, for example, for the prevention and/or treatment of haemostatic disorders associated with platelet adhesion and aggregation due to alloimmunisation.

The pharmaceutical composition may further comprise an auxiliary agent, e.g. selected from the group consisting of a pharmaceutically acceptable carrier, diluent, salt, buffer, or excipient. Said pharmaceutical composition can be used for treating the above-defined bleeding disorders. Further, the pharmaceutical composition may be administered by any route known in the prior art. In one example, the pharmaceutical composition may be administered intravenously.

The antibody as defined above can be used to neutralize an HPA as defined above in the plasma of mothers, it can be injected into the foetus or into the amniotic fluid. Moreover, the antibody as defined above can be grafted on a support like beads or polymers to deplete the HPA when the plasma is incubated with these supports during an apheresis procedure (selective plasma apheresis).

The present invention further relates to the use of the antibody as defined above in the manufacture of a medicament for the prevention and/or treatment of a primary hemostatic disorder resulting from an alloimmunisation as defined above.

The present invention also relates to a kit containing an antibody as defined above.

Additionally, the present invention relates to a kit according to the present invention for diagnostic use. In a preferred embodiment of the present invention, the diagnostic use comprises the step of detecting the presence or absence of one or more HPA in maternal blood to detect whether a pregnant mother has antibodies directed against HPA which react with fetal cells eventually causing hemolytic diseases of the newborn. In another preferred embodiment of the present invention the diagnosis comprises the step of detecting the presence or absence of one or more HPA in the blood of a donor and/or a recipient of a blood transfusion to determine, whether a blood transfusion can be carried out, i.e. pre-transfusion testing. In another preferred embodiment of the present invention the diagnosis comprises the step of detecting the presence or absence of one or more HPA in the blood of a donor and/or a recipient of an organ transplantation to determine, whether a transplantation will be successful, i.e. pre-transplantation testing. In another preferred embodiment of the present invention the diagnosis comprises the step of detecting the presence or absence of a primary hemostatic disorder resulting from an alloimmunisation as defined above.

The antibody according to the present invention can replace the polygonal human sera currently used in diagnostics and may be an instrument to investigate mechanisms that play a role in antibody mediated platelet destruction. The antibody as defined above has several advantages compared with the polyclonal sera which are dependent on rare donors and have to be extensively absorbed and purified. In particular, the antibody can be produced according to demand at a constant quality, without the batch-to-batch variation observed for antisera. In addition, diagnostic application of the antibody according to the present invention is not dependent on expertise only available at a few reference laboratories. Moreover, the antibody according to the present invention can have therapeutic applications for the prevention of neonatal alloimmune thrombocytopenia or to inhibit the adhesion and aggregation of platelets to prevent thrombosis.

Table 1 Effect of human anti-HPA-5b antibody on platelet adhesion evaluated with the PFA 100 test. Fresh blood from a HPA 5ab donor was incubated with 50 µg/ml anti-HPA-5b antibodies and compared with same concentration of fresh blood from a HPA 5aa donor This test shown that the antibody inhibits the adhesion induces by collagen.+ADP.

The present invention will now be further illustrated in the following examples without being limited thereto.

EXAMPLES

Example 1

Blood Samples, Platelets and Polyclonal Antisera

A blood sample from an alloimmunized woman (UPN 220574 MN) with a high titer of anti-HPA-5b antibodies was obtained one month after delivery. The platelets used for all experiments were homozygous for either HPA-5a (HPA-5aa) or HPA-5b (HPA-5bb) (typed by using polymerase chain reaction employing sequence specific priming (PCR-SSP) and verified by using MAIPA technique).

Example 2

Generation of EBV-transformed B Cell Lines

Peripheral blood mononuclear cells (MNC) were isolated by standard Ficoll-Hypaque gradient centrifugation. Ten to $90 \times 10^6$ blood MNC from selected donors were cultured in the CD40 system after EBV infection essentially as previously described (Peyron et al., 1994 Human monoclonal antibodies specific for bullous pemphigoid antigen (BPAg1) J Immunol 153, 1333-1339) with some modifications: MNC were seeded at 1000 to 5000 cells/well in round-bottom 96-well culture plates (Nunc, Roskilde, Denmark) together with 5000 irradiated (7000 rad) CD32-transfected L cells/well (Peltz et al., 1988 Cloned and expressed human Fc receptor for IgG mediates anti CD3 dependent lymphoproliferation J Immunol 141, 1891-1896) and 0.5 pg/ml anti-CD40 mAb 89 (Vallt et al., 1989 Serum free medium for generation and propagation of functional human cytotoxic and helper T cells clones J Immunolo Methods 72, 219-227). Cultures were performed in Yssel's modified Iscove's medium supplemented with 15% heat-inactivated FCS, 2 mM L-glutamine and 50 pg/ml gentamycin. After 10 to 15 days of culture, supernatants were collected and tested for the presence of anti-HPA-5b antibodies by a MAIPA assay. The identified positive oligoclonal cell lines were then expanded to produce supernatants for further analysis and cloned by limiting dilution with irradiated allogenic blood MNC as feeders. Supernatants of culture wells showing cell growth after 2 to 4 weeks were screened for anti-HPA-5b antibodies as described above. HuMAb X3 was purified on a protein G-Sepharose-4B affinity column after ammonium-sulfate precipitation of supernatant of X3 cells cultured in RPMI 1640 supplemented with 1×Nutridoma HU (Boehringer Mannheim, Mannheim, Germany). The clone producing the anti HPA-5b human monoclonal antibody was called HF2H11.

Example 3

SDS-PAGE and Western Blot of Anti-HPA-5b Antibody 0.5 µg of purified IgG and cell free supernatant before (load) and after protein purification (flow through) were added to 15 µl 4× reducing sample buffer, heated for 5 min. at 95° C. and analyzed on a 12% SDS-polyacrylamide gel and in a Western Blot incubated with HRP-labeled polyclonal anti-human IgG antibodies (The Binding Site Ltd., Birmingham, U.K.) and with 4-chloro-1-naphtol as chromogen (Merck, Darmstadt, Germany). 3 µl of Rainbow™ coloured molecular marker CFA 756 RPN 756 (Amersham Pharmacia Biotech) was used as the molecular weight (MW) standard. Total protein staining was performed by using Bio-Safe™ Coomassie (Bio-Rad Laboratories) according to the manufacturers instructions.

Example 4

Labeling of Anti-HPA-5b Monoclonal Antibody with HRPO for ELISA Test

Purified antibodies were labeled with horseradish peroxidase (HRPO) by using an in house technology stemming from a Schiff base reaction.

Example 5

Specificity Testing Human Anti-HPA-5b by Immunodot-assay and by Monoclonal Antibody Specific Immobilization of Platelet Antigen (MAIPA) Assay To determine the specificity of anti-HPA-5b antibodies an immunodot-assay was performed.

MAIPA assay was performed as described by Kiefel et al., Blood. 1987; 70:1722-1726. Briefly, mouse anti-GPIa/IIa monoclonal antibody (Gi9, anti-CD49b, Immunotech, France) was incubated with typed platelets ($25 \times 10^7$/ml) and anti-HPA-5b (225 µg/ml) in PBS/EDTA/0.1% bovine serum albumin (BSA). The platelets were then lysed and immobilized on microtiter plates pre-coated with goat anti-mouse IgG (Jackson ImmunoResearch, USA). After extensive washing with TBS-washing buffer (Tris buffered saline at pH 7.4 containing 2% Triton X-100 and 0.1% Tween 20) bound anti-HPA-5b was detected by incubation with anti-human IgG-HRP (Jackson ImmunoResearch, USA) and addition of 100 µl substrate solution (3.5 mg tablets 1,2 O-phenylenediamine-dichloridrate (Dako Diagnostics AG, Switzerland) dissolved in 12 ml distilled water and 5 ml 30% $H_2O_2$ (added immediately before use).

Chromogenic reaction was stopped after 15-20 min by addition of 0.5 M $H_2SO_4$ and absorbance was measured at $\lambda$=490 nm.

Example 6

HPA-5b Expression on Platelets Assessed by Flow Cytometry

Fresh, non-activated platelets were isolated from 9 ml human blood and anti-coagulated using 1 ml sodium-citrate 3.8% at pH 5.5. Platelets were separated from the plasma using CL-2B sepharose (Amersham Pharmacia Biotech, Switzerland). Recombinant human anti-HPA-5b or thrombin (Becton Dickinson, Switzerland) as positive control were added to platelets ($5 \times 10^7$ cells/ml) in HEPES/BSA 0.1%. Platelets were then stained with the HF2H11 monoclonal antibody in HEPES containing $CaCl_2$ (2 mM) and $MgCl_2$ (1 mM). After incubation for 15 minutes at 37° C., platelets were washed in PBS 0.1% BSA. After washing, platelets were incubated with an anti human IgG FITC for 30 minutes and analyzed by flow cytometry on a FACScan (FACSCalibur, Becton Dickinson, San Jose, Calif., USA) using Cell Quest software (Becton Dickinson, San Jose, Calif., USA). Platelets were gated based on forward and side scatter.

Example 7

Inhibition of Aggregation

The platelet aggregation test uses an aggregometer (Servibio) to measure the cloudiness (turbidity) of blood plasma. The addition of collagen (6.5 µg/ml to a plasma sample causes the platelets to clump together, making the fluid more transparent. The aggregometer then measures the increased light transmission through the specimen.

The test was done without addition of HF2H11 antibody and in presence of antibody at various concentrations. The aggregometer record the turbidity and the time after addition of collagen. Several parameters are calculated: percentage of inhibition in comparison to the control (without antibody), the lag time and the velocity of aggregation.

Example 8

Inhibition of Adhesion

The PFA-100 test (Dade Behring) measures the time taken for blood, drawn through a fine capillary, to block a membrane coated with collagen and epinephrine (CEPI) or collagen and ADP (CADP). This is referred to as the Closure Time (CT) and is measured in seconds. The test is therefore a combined measure of platelet adhesion and aggregation. The test was done without addition of HF2H11 antibody and in presence of antibody at various concentrations.

Example 9

Specificity of Monoclonal Antibody for Native HPA-5b in MAIPA-assay

Binding of the anti HPA-5b to native HPA-5b on whole platelets was tested in an ELISA and showed strong binding to HPA-5bb or 5ab platelets and no binding to HPA-5aa platelets (FIG. 1).

Example 10

Production and Purification of the IgG1 Antibodies Specific for HPA-5b

Figure 2:
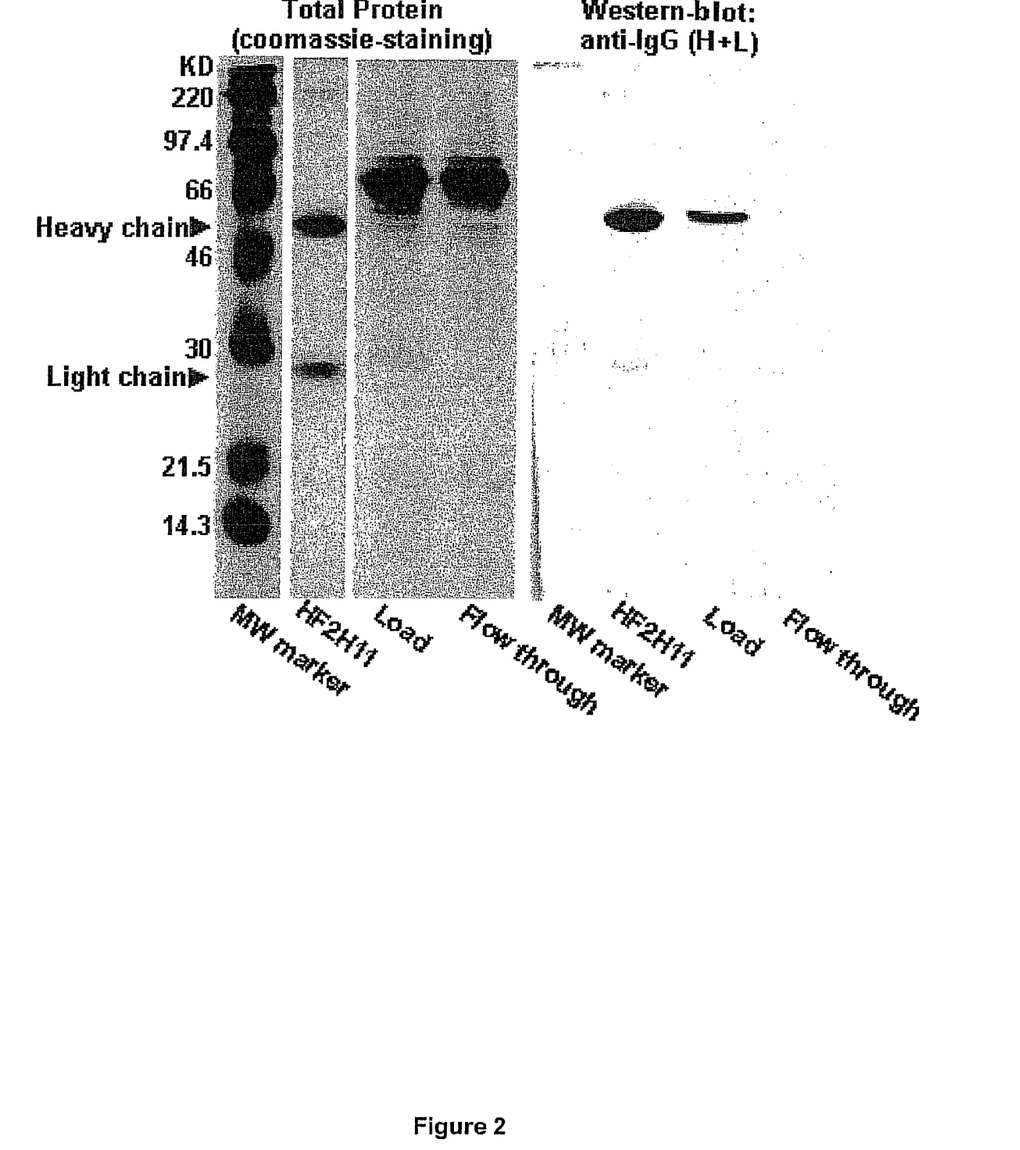
FIG. 2 illustrates SDS-PAGE and Western Blot analysis of purification of full-length human anti-HPA-5b antibody. Full-length human anti-HPA-5b antibody was purified by protein G affinity chromatography. Load (cell free supernatant), flow through and purified anti-HPA-5b IgG were analyzed on a 12% SDS-polyacrylamide gel and in a Western Blot under reducing conditions. Immunoglobulin heavy and light chain were detected by a polyclonal anti-HuIgG antibody conjugated to HRP. Total protein was analyzed by staining the gel with Coomassie-blue.
Figure 3:
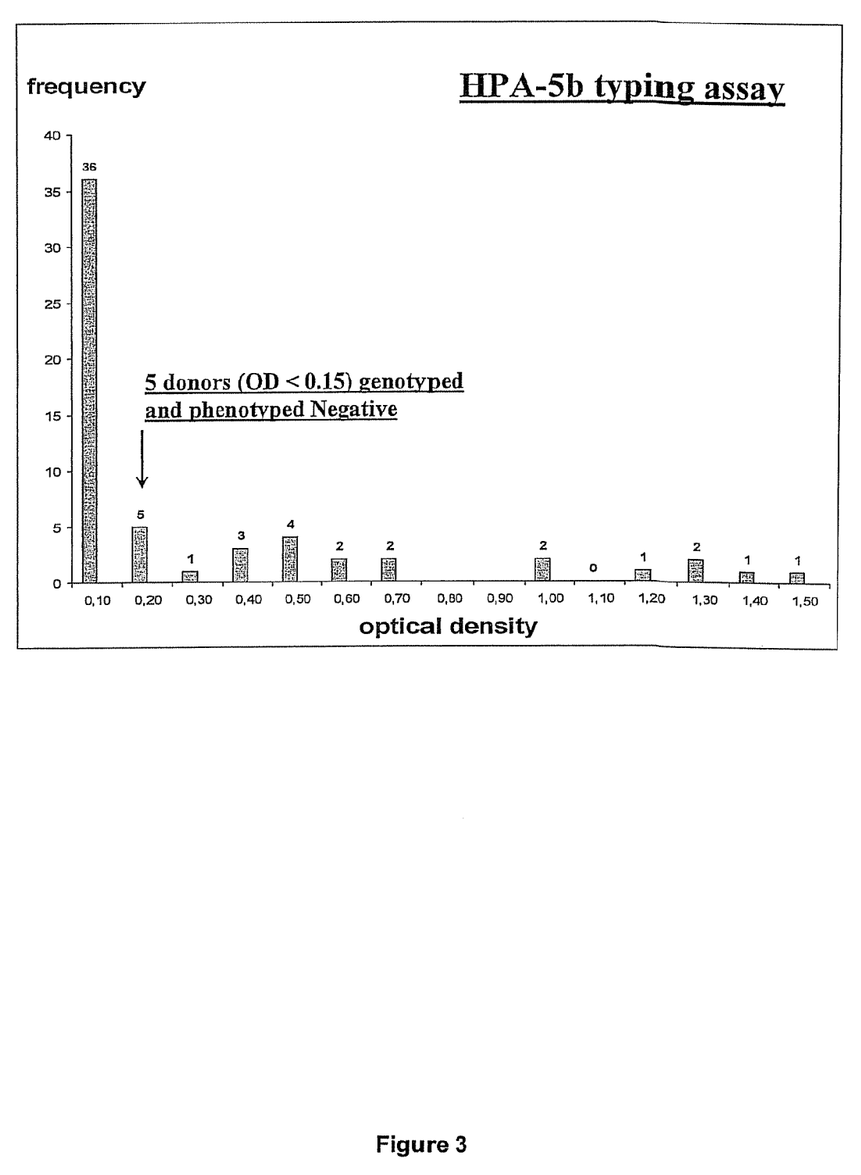
FIG. 3 illustrates the specificity human anti-HPA-5b antibodies by comparing the monoclonal antibody HF2H11 and anti-serum (polyclonal human anti-HPA-5b antibodies). 50 donors and 10 panel platelets tested in 2 techniques; 38 donors genotyped HPA-5b negative and 12 HPA-5b positive 3 panel platelets known HPA-5b negative, 7 HPA-5b positive.

The HF2H11b cell line was cultured in DEMF12+10% FCS by using two systems. The first one is called "stationary culture" and was performed in 50 ml flask (Falcon). The second one was performed in high density devices (Integra cell line 1000 from IBS Integra). Cell free supernatant was harvested ten days after seeding and IgG was purified using protein G sepharose. SDS-PAGE and Western Blot analysis showed excellent separation and purification of the recombinant IgG from other proteins as shown in FIG. 2. The yield of antibody production was up to 10 mg per liter supernatant for the stationary technique and up to 1000 mg per liter for the high density technology.

Example 11

Testing the Specificity of the Anti HPA-5B on Typed Platelets

Human anti-HPA-5b antibodies were labeled with HRPO and tested in immunodot-assay on platelets for binding to HPA-5b. In order to monitor variation of the amount of GPIa/IIa expressed on platelets from different donors we used an anti-GPIa/IIa antibody that bound equally to 'a' and 'b' alleles. As reference, the extensively absorbed and purified polyclonal human anti-HPA-5b serum was analyzed in the same assay. Human polyclonal IgG was used to check for antigen-unrelated binding of immunoglobulins to Fcγ receptors on platelets as control. The human anti-HPA-5b antibody could discriminate between HPA-5aa and HPA-5bb platelets equally well as the polyclonal human anti-HPA-5b serum. In view of the low antigen expression of HPA-5, a titration increasing the amount of platelets with a constant concentration of antibody was performed. A strong dependence on antigen concentration evident in FIG. 2 indicates, that antigen

Example 12

Performance of Human Monoclonal Anti-HPA-5b Antibody Using MAIPA Technique

Figure 4:
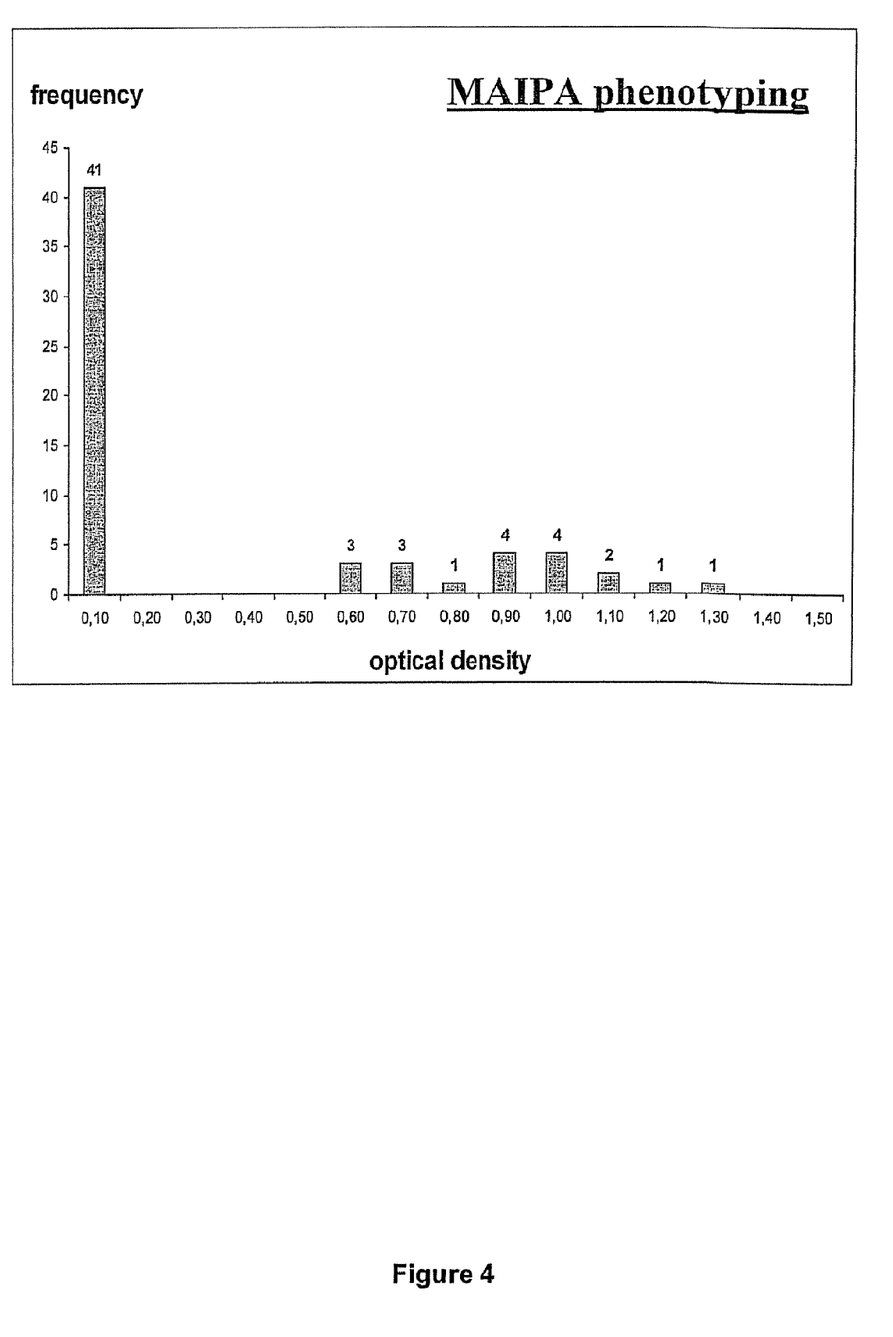

The MAIPA assay is a standard method currently used for platelet alloantigen/alloantibody diagnostics and is limited to a few specialized laboratories. This method depends on a source of polyclonal human antisera extensively absorbed and purified such that there is a selective recognition of HPA-5b on platelets. To perform the MAIPA assay, the human anti-HPA-5b antibody HF2H11 was incubated with platelets and a mouse monoclonal anti-GPIa/IIIa antibody. Platelets were then lysed and immobilized on anti-mouse-IgG coated microtiter plates. The assay was developed using anti-human IgG-HRP antibodies. The experiment was repeated six times using platelets from different donors. The recombinant anti-HPA-5b antibody clearly discriminates between HPA-5a and HPA-5b, with no binding to HPA-5aa platelets (FIG. 4).

Example 13

Physiological Effects of Monoclonal Human Anti-HPA-5b on Fresh Non-activated Platelets Integrins such as the collagen receptor located on GPIa are involved in platelet activation and formation of platelet aggregates. Antibodies binding to an alloantigen (HPA-5a/b) located in the vicinity of the collagen receptor might show a capacity to activate platelets. In order to test this possibility, fresh non-activated platelets were mixed for 15 minute at 37° C. with the anti-HPA-5b antibody HF2H11 and activation of platelets was determined by measurement of the upregulation of CD62 (P-selectin) an early marker of platelet activation was assessed by flow cytometry.

Figure 6:
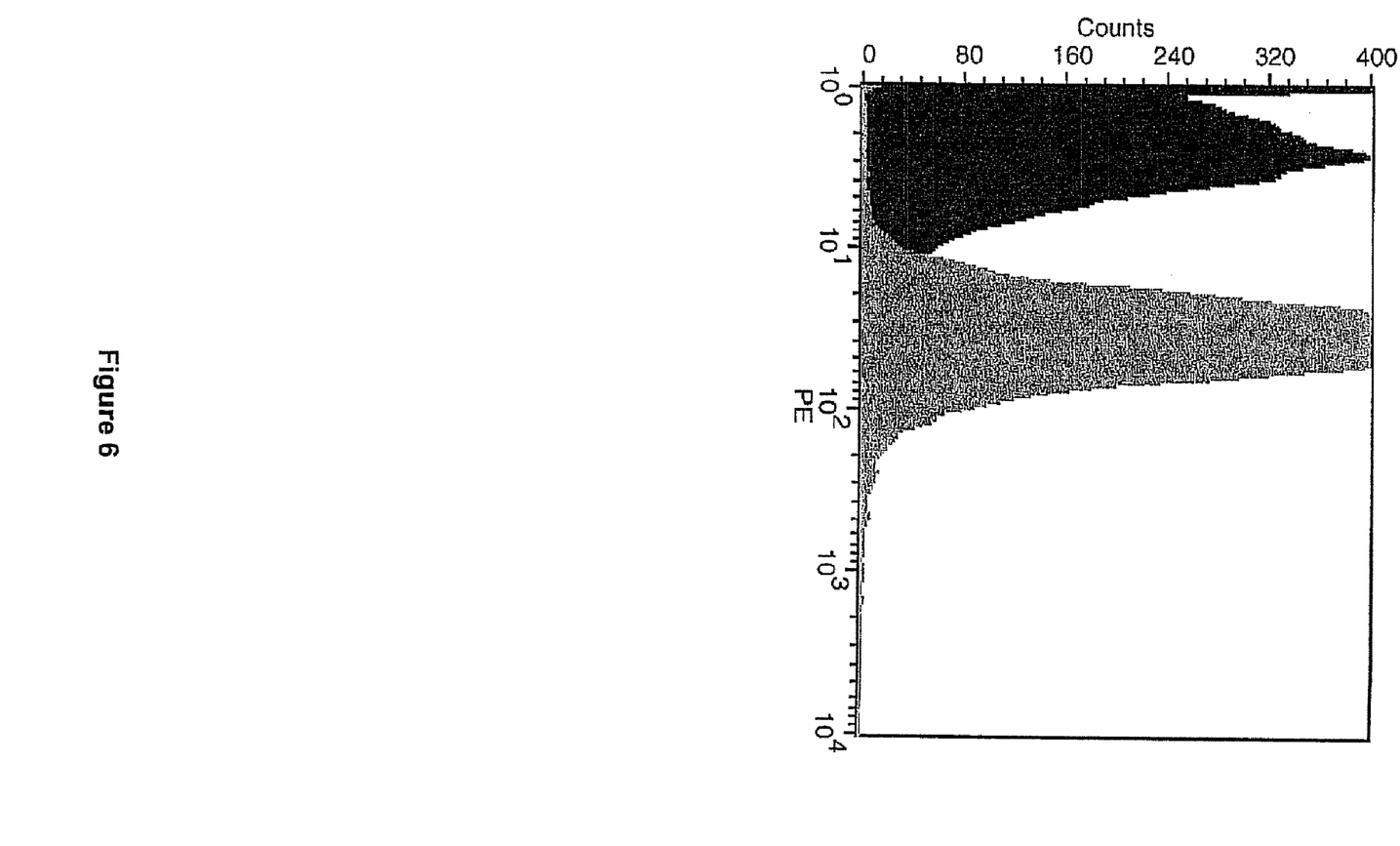
FIG. 6 illustrates flow cytometer analysis of platelets labelled with the HF2H11 antibody. Labelling of HPA-5b− (black) and HPA-5b+(grey) platelet with anti-human monoclonal antibody HF2H11 specific for HPA-5b epitope.

Human anti-HPA-5b antibodies bound to the platelets (data not shown) but did not activate them in contrast to thrombin used as a positive control (FIG. 6).

Example 14

Effect of Human Anti-HPA-5b Antibody on Platelet Aggregation

Figure 5:
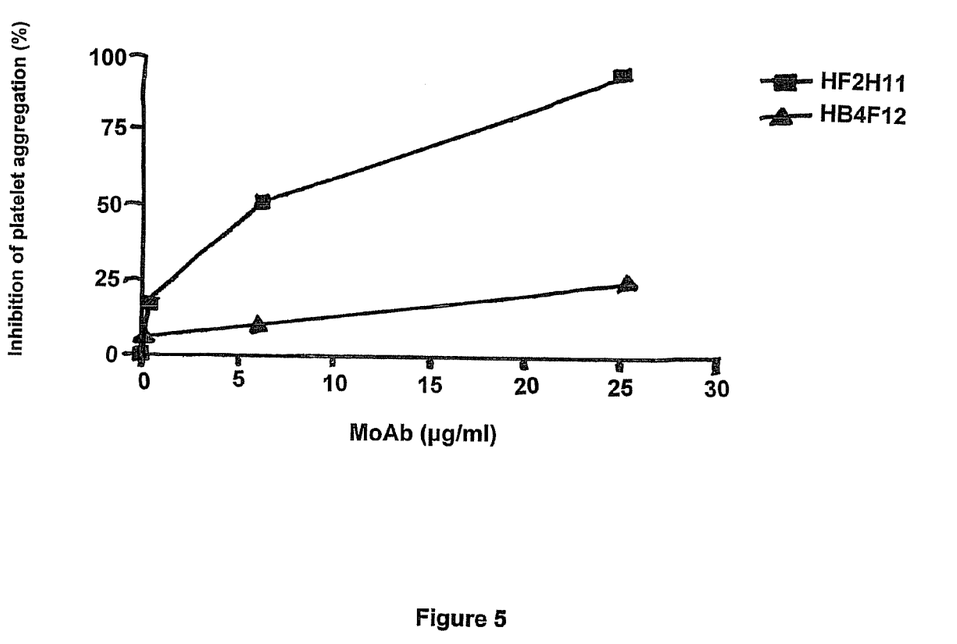
FIG. 5 illustrates the effect of human anti-HPA-5b antibody on Platelet aggregation. Fresh non-activated platelets were incubated with 0.25, 6.25 or 25 .mu.g/ml anti-HPA-5b antibodies (squares) and compared with same concentration of unrelated antibody (triangles). This test shown that the antibody inhibits the aggregation induces by collagen.

Fresh non-activated platelets ($5 \times 10^7$/ml) were incubated with 0.25, 6.25 or 25 mg/ml anti-HPA-5b antibodies (squares) and compared with same concentration of unrelated antibody (triangles). This test shows that the antibody inhibits the aggregation induced by collagen. FIG. 5 shows that the antibody inhibits aggregation by 80% when using 25 µg/ml.

Example 15

Effect of Human Anti-HPA-5b Antibody on Platelet Adhesion

This effect was evaluated with the PFA 100 test. Fresh blood from a HPA 5ab donor was incubated with 50 mg/ml anti-HPA-5b antibodies and compared with same concentration of fresh blood from a HPA 5aa donor. This test shows that the antibody inhibits the adhesion induced by collagen+ADP (Table 1).

In conclusion, we were able to isolate fully human anti-HPA-5b antibodies using B lymphocytes stimulation by using anti CD 40 antibodies and immortalisation by using EBV. HF2H11 antibody was produced as full-length IgG1 antibodies and can be used to distinguish between 'a' and 'b' alleles of HPA-5.

TABLE 1

| Test with HPA-5ab platelets | | | |
| --- | --- | --- | --- |
| HF2H11 | 0 µg/ml | Coll + ADP | PFA-100 = 141 sec |
| HF2H11 | 50 µg/ml | Coll + ADP | PFA-100 > 300 sec |
| Test with HPA-5aa platelets | | | |
| HF2H11 | 0 µg/ml | Coll + ADP | PFA-100 = 128 sec |
| HF2F11 | 50 µg/ml | Coll + ADP | PFA-100 = 162 sec |
| Normal values: 94-194 sec | | | |

What is claimed:

1. An isolated monoclonal antibody HF2H11 or a binding fragment thereof that binds specifically to human platelet alloantigen HPA-5b.

2. A composition comprising the antibody or the binding fragment thereof according to claim 1.

3. A kit containing the antibody or the binding fragment thereof according to claim 1.

* * * * *